United States Patent [19]

Cohen

[11] Patent Number: 5,840,747
[45] Date of Patent: Nov. 24, 1998

[54] CALCIUM CHANNEL ANTAGONISTS

[75] Inventor: Marlene L. Cohen, Carmel, Ind.

[73] Assignee: Eli Lilly and Company, Indianapolis, Ind.

[21] Appl. No.: 485,406

[22] Filed: Jun. 7, 1995

[51] Int. Cl.$^6$ ................................................ A61K 31/445
[52] U.S. Cl. ......................... 514/443; 514/320; 514/324; 514/317
[58] Field of Search .................................... 514/317, 324, 514/320, 443

[56] References Cited

U.S. PATENT DOCUMENTS

| | | | |
|---|---|---|---|
| 4,133,814 | 1/1979 | Jones et al. | 424/267 |
| 4,418,068 | 11/1983 | Jones | 424/267 |
| 5,447,941 | 9/1995 | Zuckerman | 514/324 |

OTHER PUBLICATIONS

Collins et al., "Cardiovascular Protection by Oestrogen—A Calcium Antagonist Effect?", *Lancet,* 341, 1264–65 (1993).
Jiang et al., "Endothelium–Independent Relaxation of Rabbit Coronary Artery by 17β–Oestradiol In Vitro", *Br. J. Pharmacol.,* 104, 1033–37 (1991).
Stice et al., "Interaction of 4–Hydroxylated Estradiol and Potential–Sensitive $Ca^{2+}$ Channels in Altering Uterine Blood Flow during the Estrous Cycle and Early Pregnancy in Gilts", *Biology of Reproduction,* 36, 369–75 (1987).
Batra, "Influence of Chronic Oestrogen Treatment on the Density of Muscarinic Cholinergic Receptors and Calcium Channels in the Rabbit Uterus", *J. Endocrin.,* 125, 185–188 (1990).
Wren, "The Effect of Oestrogen on the Female Cardiovascular System", *Med. J. of Australia,* 157, 204–208, (1992).
Zhang et al., "Sexual Dimorphism of Vascular Smooth Muscle Responsiveness is Dependent on Anions and Estrogen", *Steroids,* 56, 524–526 (1991).
(CA) 95–225,950: Zuckerman, "Use of 2–phenyl–benzothiophene Cmpds. Such as Raloxifene—for Inhibiting Pulmonary Hypertensive Disease" EP 659426 95/06128. Abstract Only.

*Primary Examiner*—Keith D. MacMillan
*Attorney, Agent, or Firm*—Janelle D. Strode; David E. Boone

[57] ABSTRACT

A method for antagonizing or blocking calcium channels in vascular tissue, comprising administering to an animal in need thereof a pharmaceutically-effective amount of a compound having the formula

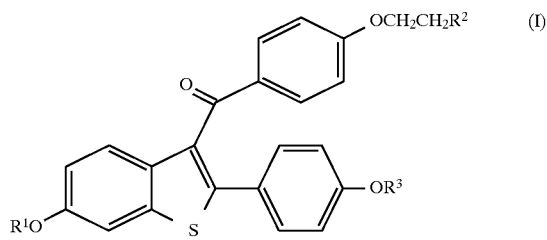

wherein $R^1$ and $R^3$ are independently hydrogen, $C_1$–$C_4$ alkyl, —CO—($C_1$–$C_6$ alkyl), or —$CH_2$Ar, —CO—Ar, wherein Ar is phenyl or substituted phenyl;
$R^2$ is selected from the group consisting of pyrrolidine, hexamethylenemino, and piperidino; or a pharmaceutically-acceptable salt thereof.

14 Claims, 8 Drawing Sheets

CALCIUM CHANNEL ANTAGONISTS

BACKGROUND OF THE INVENTION

This invention relates to the discovery that a group of 2-aryl-3-aroylbenzo[b]thiophenes are calcium channel antagonists in vascular tissue.

Replacement therapy with estrogen is generally acknowledged to produce beneficial effects on the cardiovascular system in postmenopausal women. See Knopt, *Obstet. Gynecol.*, 72, 23s–30s (1988). In postmenopausal women who receive estrogens, the cardiovascular mortality rate is reduced by about 30% to about 50%, and the cerebrovascular mortality rate is reduced by about 50%. See Stampfer et al., *N. Engl. J. Med.*, 325, 756–762 (1991). Although these beneficial cardiovascular effects may involve alterations in lipid profile, recent data suggests that estrogen may also have beneficial effects on the vascular responses of atherosclerotic coronary arteries. See Gisclard et al., *J. Pharmacol. and Experimental Therapeutics*, 244, 19–22 (1988); Williams et al., *Circulation*, 81, 1680–1687 (1990); Gangar et al., Lancet, 388, 839–842 (1991); and Williams et al., *JACC*, 20, 452–457 (1992). Both endothelial-independent and endothelial-dependent effects of estrogen have been described in vascular tissue. See Jiang et al., Br. *J. Pharmacol.*, 104, 1033–1037 (1991); Jiang et. al., *American Journal of Physiology*, 32, H271–H275 (1992); Cheng and Gruetter, *European Journal of Pharmacol.*, 215, 171–176 (1992); Mügge et al., *Cardiovas. Res.*, 27, 1939–1942 (1993); Salas et al., *European Journal of Pharmacol.*, 258, 47–55 (1994); Williams et al., *Circulation*, 81, 1680–1687 (1990); Cheng et al., *Life Sciences*, 10, 187–191 (1994); Gilligan et al., *Circulation*, 89, 2545–2551 (1994); and Reis et al., *Circulation*, 89, 52–60 (1994). Several reports have also suggested that the vasodilating effects of estradiol and/or its ability to attenuate contractile responses may be mediated by inhibition of calcium influx via voltage dependent calcium channels. See Jiang et al., Br. *J. Pharmacol.*, 104, 1033–1037 (1991); Jiang et. al., *American Journal of Physiology*, 32, H271–H275 (1992); Collins et al., *Lancet*, 341, 1264 (1993); Muck et al., *Med. Sci. Res.*, 22, 19 (1994); and Salas et al., *European Journal of Pharmacol.*, 258, 47–55 (1994). Others have postulated that estradiol may enhance cyclic AMP and cyclic GMP content, or increase ATP-sensitive potassium channels. See Mügge et al., *Cardiovas. Res.*, 27, 1939–1942 (1993).

The 2-aryl-3-aroylbenzo[b]thiophene compounds that are used in the methods of this invention were first developed by Jones and Suarez as anti-fertility agents. See U.S. Pat. No. 4,133,814 (issued Jan. 9, 1979). These compounds are generally useful in suppressing the growth of mammary tumors. Jones later found that a group of these compounds are particularly useful for antiestrogen and antiandrogen therapy, especially in the treatment of mammary and prostatic tumors. See U.S. Pat. 4,418,068 (issued Nov. 29, 1983). One of these compounds, 6-hydroxy-2-(4-hydroxyphenyl)-3-[4-(2-piperidinoethoxy)benzoyl]benzo[b]thiophene was clinically studied for the treatment of breast cancer. This compound is called raloxifene, formerly keoxifene.

SUMMARY OF THE INVENTION

This invention provides methods for antagonizing or blocking calcium channels in vascular tissue, comprising administering to a warm-blooded animal in need thereof an effective amount of a compound of the formula

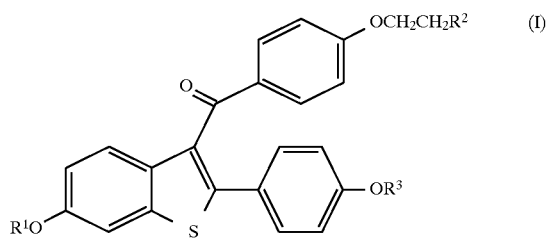

wherein $R^1$ and $R^3$ are independently hydrogen, $C_1$–$C_4$ alkyl, —CO—($C_1$–$C_6$ alkyl), —$CH_2$Ar, or —CO—Ar, wherein Ar is phenyl or substituted phenyl;

$R^2$ is selected from the group consisting of pyrrolidino, hexamethyleneimino, and piperidino; or a pharmaceutically-acceptable salt thereof. The present invention also provides the use of the formula I compounds, or pharmaceutically-acceptable salts thereof, for the manufacture of a medicament for antagonizing or blocking calcium channels in vascular tissue.

DETAILED DESCRIPTION OF THE INVENTION

Figure 1:
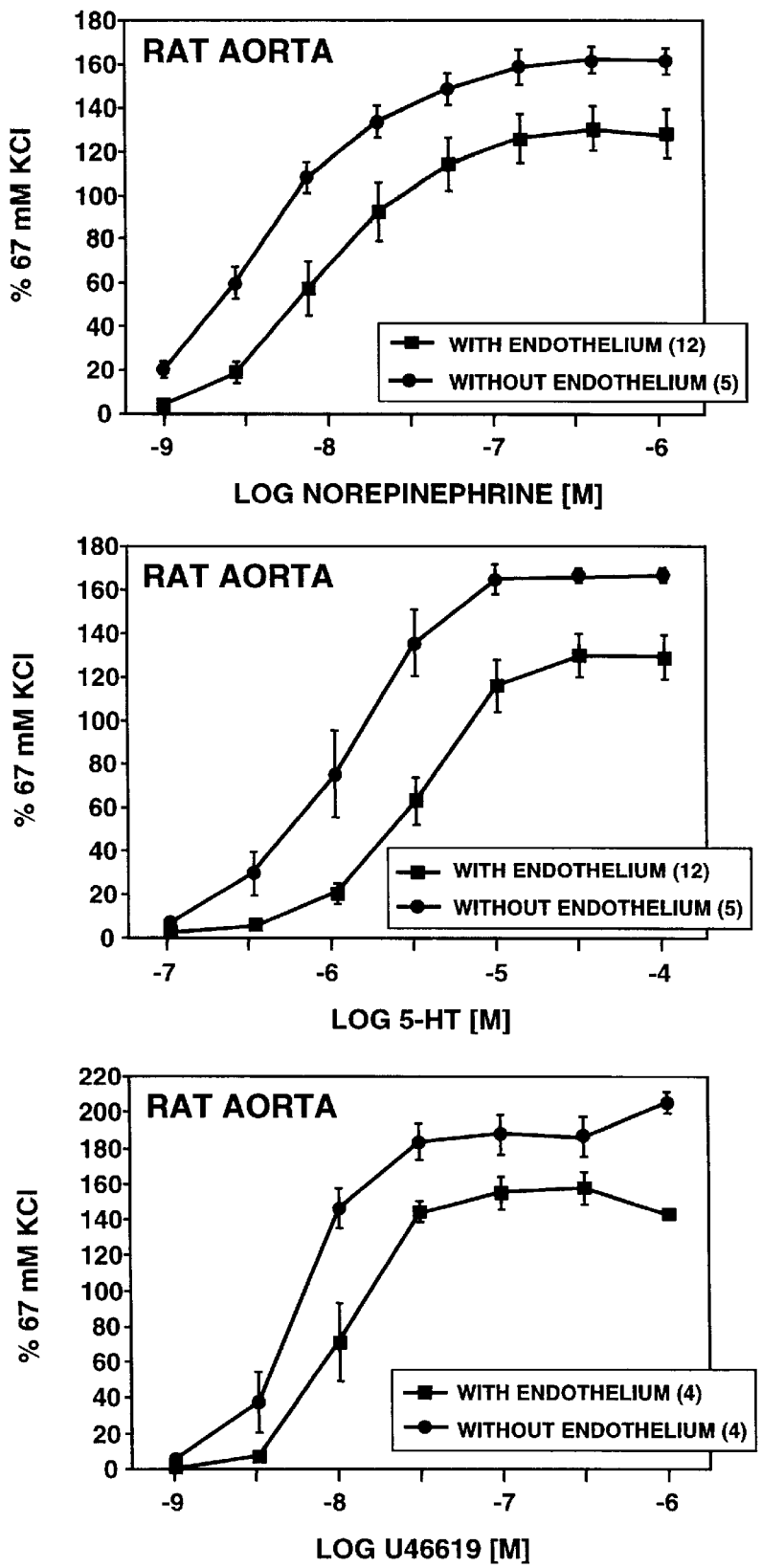
FIG. 1: Contractile responses to norepinephrine (top), serotonin (middle), and U46619 (bottom) in rat aortic rings in the presence and absence of the endothelium. Endothelium integrity was measured by challenge with acetylcholine as indicated in the methods. Points are mean values and vertical bars represent the standard error of the mean for the number of rings indicated in parenthesis.

The present invention concerns the discovery that a select group of 2-aryl-3-aroylbenzo[b]thiophenes (benzo[b]thiophenes), the compounds of formula I, are calcium channel antagonists. Therefore, the present invention provides methods for antagonizing or blocking calcium channels in vascular tissue. One aspect of the invention is a method for treating cardiac disorders, including but not limited to variant angina, exertional angina, unstable angina, ischemia-reperfusion injury to the myocardium, and arrhythmias. Another aspect is a method for treating cerebral vascular disorders, including but not limited to cerebral vasospasm due to arterial rupture, stroke, and migraine headaches. Another aspect is a method for treating renal disorders by increasing renal clearance due to increases in renal blood flow, useful for slowing of renal failure. Another aspect is a method for treating gastrointestinal disorders, including but not limited to diseases related to diarrhea, such as IBS and IBD, diarrhea predominant. Another aspect is a method for treating hypertension. The therapeutic treatments provided by this invention are practiced by administering to a warm-blooded animal in need thereof a pharmaceutically-effective amount of a compound of formula I or a pharmaceutically-acceptable salt thereof.

In the above formula, the term "$C_1$–$C_6$ alkyl" represents a straight, cyclic, or branched alkyl chain having from one to six carbon atoms. Typical $C_1$–C6 alkyl groups include methyl, ethyl, n-propyl, isopropyl, n-butyl, isobutyl, sec-butyl, t-butyl, n-pentyl, isopentyl, n-hexyl, cyclopropyl, cyclobutyl, cyclopentyl, cyclohexyl, and the like. The term "$C_1$–$C_4$ alkyl" represents a straight or branched alkyl chain having one to four carbon atoms. Typical $C_1$–$C_4$ alkyl groups include methyl, ethyl, n-propyl, isopropyl, n-butyl, secbutyl, isobutyl, and t-butyl.

The term "Ar" represents groups such as phenyl and substituted phenyl. The term "substituted phenyl", as used herein, represents a phenyl group substituted with one or more moieties chosen from the group consisting of halogen, hydroxy, cyano, nitro, $C_1$–$C_4$ alkyl, $C_1$–$C_4$ alkoxy, acetyl, formyl, trichloromethyl, or trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 4-cyanophenyl, 4-methylphenyl, 4-ethylphenyl, 4-methoxyphenyl, 4-propylphenyl, 4-n-butylphenyl, 4-t-butylphenyl, 3-fluoro-2-methylphenyl, 2,3-difluorophenyl, 2,6-difluorophenyl, 2,6-dimethylphenyl, 2-fluoro-5-methylphenyl, 2,4,6-trifluorophenyl, 2-trifluoromethylphenyl, 2-chloro-5-trifluoromethylphenyl, 3,5-bis(trifluoromethyl)phenyl, 2-methoxyphenyl, 3-methoxyphenyl, 3,5-dimethoxyphenyl, 4-hydroxy-3-methylphenyl, 3,5-dimethyl-4-hydroxyphenyl, 2-methyl-4-nitrophenyl, 4-methoxy-2-nitrophenyl, 2,4-dinitrophenyl, and the like. The term "$C_1$–$C_4$ alkoxy" represents groups such as methoxy, ethoxy, n-propoxy, isopropoxy, n-butoxy, t-butoxy, and the like. The term "halogen" represents fluoro, chloro, bromo, and iodo.

The term "blocking" or "antagonizing" indictes that the formula I compounds bind to the calium channels in the vascular tissue and thereby inhibit the flux of calcium.

The term "pharmaceutically-effective amount" is used herein to represent an amount of the formula I compound that is capable of antagonizing or blocking calcium channels in vascular tissue. The particular dose of the formula I compound will of course be determined by the particular circumstances surrounding the case, including the compound administered, the route of administration, the particular condition treated, and similar considerations.

The term "warm-blooded animal", as used herein, includes humans; companion animals, such as dogs and cats; and domestic animals, such as horses, cattle, sheep, swine, goats and chickens. Preferably, the warm-blooded animal is a human or companion animal. More preferably, the warm-blooded animal is a human.

While all the formula I compounds are useful for antagonizing or blocking calcium channels in vascular tissue, certain compounds are preferred. Preferably, $R^1$ and $R^3$ are independently hydrogen, $C_1$–$C_4$ alkyl, —CO—($C_1$–$C_6$ alkyl), or benzyl, and $R^2$ is piperidino or pyrrolidino. Representative compounds from this preferred group include 6-hydroxy-2-(4-hydroxyphenyl)-3-[4-(2-pyrrolidinoethoxy)benzoyl]-benzo[b]thiophene, 6-methoxy-2-(4-methoxyphenyl)-3-[4-(2-piperidinoethoxy)benzoyl]benzo[b]thiophene, 6-acetoxy-2-(4-acetoxyphenyl)-3-[4-(2-pyrrolidinoethoxy)benzoyl]-benzo[b]thiophene, and 6-benzyloxy-2-(4-benzyloxyphenyl)-3-[4-(2-piperidinoethoxy)benzoyl]-benzo[b]thiophene.

More preferably, $R^1$ and $R^3$ are independently hydrogen or $C_1$–$C_4$ alkyl, and $R^2$ is piperidino or pyrrolidino. Representative compounds from this more preferred group include 6-hydroxy-2-(4-hydrophenyl)-3-[4-(2-pyrrolidinoethoxy)benzoyl]benzo[b]thiophene, 6-hydroxy-2-(4-hydroxyphenyl)-3-[4-(2-piperidinoethoxy)benzoyl]benzo[b]thiophene, 6-methoxy-2-(4-methoxyphenyl)-3-[4-(2-pyrrolidinoethoxy)benzoyl]benzo[b]thiophene, and 6-methoxy-2-(4-methoxyphenyl)3-[4-(2-piperidinoethoxy)benzoyl]benzo[b]thiophene. Most preferably, $R^1$ and R3 are hydrogen and $R^2$ is pyrrolidino. This most preferred compound is 6-hydroxy-2-(4-hydroxyphenyl)-3-[4-(2-pyrrolidinoethoxy)benzoyl]benzo[b]thiophene.

The formula I compounds used in the methods of the present invention can be made according to established procedures, such as those described in U.S. Pat. Nos. 4,133,814, 4,418,068, and 4,380,635, all of which are incorporated by reference herein. In general, the process starts with 6-hydroxy-2-(4-hydroxyphenyl)benzo[b]thiophene. This starting compound is protected, acylated at C-3 with a 4-(2-aminoethoxy)benzoyl group, and optionally deprotected to form the formula I compounds. Examples of the preparation of such compounds are provided in the U.S. Patents discussed above.

The compounds used in the methods of this invention form pharmaceutically-acceptable acid and, wherein $R^1$ and/or $R^3$ is hydrogen, base addition salts with a wide variety of organic and inorganic acids and bases, including the physiologically-acceptable salts which are often used in pharmaceutical chemistry. Typical inorganic acids used to form such salts include hydrochloric, hydrobromic, hydriodic, nitric, sulfuric, phosphoric, hypophosphoric, and the like. Salts derived from organic acids, such as aliphatic mono- and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically-acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, and β-hydroxybutyrate, butyne- 1,4-dioate, hexyne-1,6-dioate, caprate, caprylate, chloride, cinnamate, citrate, formate, fumarate, glycolate, heptanoate, decanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartrate, and the like. The most preferred salt is the hydrochloride salt.

The pharmaceutically-acceptable acid addition salts are typically formed by reacting a compound of formula I with an equimolar or excess amount of acid. The reactants are generally combined in an organic solvent such as methanol, diethyl ether, or benzene. The salt normally precipitates out of solution within about one hour to 10 days and can be isolated by filtration, or the solvent can be stripped off by conventional means.

Bases commonly used for formation of salts include ammonium hydroxide and alkali and alkaline earth metal hydroxides, carbonates, as well as aliphatic primary, secondary, and tertiary amines, and aliphatic diamines. Bases especially useful in the preparation of addition salts include ammonium hydroxide, potassium carbonate, methylamine, diethylamine, ethylenediamine, and cyclohexylamine. These salts are generally prepared by reacting a formula I compound, wherein $R^1$ and/or $R^3$ are hydrogen, with one of the above bases in an organic solvent, such as methanol, diethyl ether, or benzene. The salts are isolated as described in the preceding paragraph.

These pharmaceutically-acceptable salts generally have enhanced solubility characteristics compared to the compound from which they are derived, and thus are often more amenable to formulation as liquids or emulsions.

The formula I compounds are preferably formulated prior to administration such as in a pharmaceutical formulation comprising a compound of formula I and a pharmaceutically-acceptable carrier, diluent, or excipient. These pharmaceutical formulations are prepared by known procedures using well-known and readily available ingredients. in making these compositions, the active ingredient will usually be mixed with a carrier, diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example up to 10% by weight of active compound, soft and hard gelatin capsules, dermal patches, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, micro-crystalline cellulose, polyvinylpyrrolidone, cross-linked polyvinylpyrrolidone, cellulose or derivatives thereof, water syrup, methyl cellulose, methyl and propyl hydroxybenzoates, talc, magnesium sterate and mineral oil.

The formulations can additionally include lubricating agents, wetting agents (e.g. surfactant), emulsifying and suspending agents, disintegrating agents, preserving agents, sweetening agents, or flavoring agents. Compositions of the inventions may be formulated so as to provide quick, sustained, or delayed release of the active ingredient after administration to the patient by employing procedures well known in the art.

The particular dosage of a compound of formula I required for antagonizing or blocking calcium channels in vascular tissue, according to this invention, will depend upon the severity of the condition, the route of administration, and related factors that will be decided by the attending physician. Generally, effective daily doses will be from about 0.1 to about 1000 mg/day, and more typically from about 50 to about 250 mg/day. Such dosages will be administered to a subject in need thereof from once to about three times each day, or more often as needed to effectively treat the condition or symptom.

It is usually preferred to administer a compound of formula I in the form of an acid addition salt, as is customary in the administration of pharmaceuticals bearing a basic group, such as the piperidino group. For such purposes the following oral dosage forms are available.

Formulations

In the formulations which follow, "Active ingredient" means a compound of formula I.

Formulation 1: Gelatin Capsules

Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene capsule

| Ingredient | Quantity (mg/capsule) |
|---|---|
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
|---|---|
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
|---|---|
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
|---|---|
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

Formulation 7: Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

Formulation 8: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Illustrative compounds that can be used in the methods of the present invention are shown in Table 1.

TABLE 1

| Compound No | $R^1$ and $R^3$ | $R^2$ | Form |
|---|---|---|---|
| 1 | —C(O)—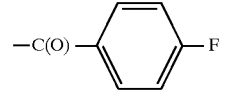—F | piperidino | base |
| 2 | —C(O)—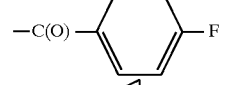—F | piperidino | HCl |
| 3 | —C(O)— | piperidino | base |
| 4 | —C(O)—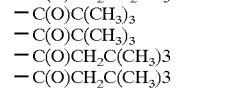 | piperidino | HCl |
| 5 | —C(O)CH$_2$CH$_2$CH$_3$ | piperidino | base |
| 6 | —C(O)CH$_2$CH$_2$CH$_3$ | piperidino | HCl |
| 7 | —C(O)C(CH$_3$)$_3$ | piperidino | base |
| 8 | —C(O)C(CH$_3$)$_3$ | piperidino | HCl |
| 9 | —C(O)CH$_2$C(CH$_3$)3 | piperidino | base |
| 10 | —C(O)CH$_2$C(CH$_3$)3 | piperidino | HCl |
| 11 | —C(O)—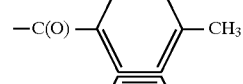—CH$_3$ | piperidino | HCl |
| 12 | —C(O)—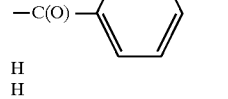 | piperidino | base |
| 13 | H | piperidino | base |
| 14 | H | piperidino | HCl |
| 15 | H | pyrrolodino | base |
| 16 | H | pyrrolodino | HCl |
| 17 | H | hexamethyleneimino | HCl |
| 18 | CH$_3$ | piperidino | HCl |

The utility of the compounds of formula I is illustrated by the positive impact they have in at least one of the experiments described below.

Methods

Male Wistar rats (250–350 g; Charles River Laboratories, Portage, Mich.) were sacrificed by cervical dislocation. The aorta was removed and cleaned of extraneous tissue and cut into ring segments, each approximately 4–5 mm long. In some tissues, endothelium was removed by rotating the ring segment around the tip of a forceps 10 times. Lack of tissue relaxation to acetylcholine ($10^{-6}$M) after contraction with norepinephrine ($10^{-7}$M) was used as evidence for denuded endothelium. Tissues with an intact endothelium relaxed to acetylcholine with 88.5±1.6% (n–11) relaxation.

Ring segments were placed between two stainless steel hooks and mounted in isolated organ baths containing 10 ml of modified Krebs' bicarbonate buffer of the following composition (mM): NaCl, 118.2; KCl, 4.6' $CaCl_2.2H_2O$, 1.6; $KH_2PO_4$, 1.2; $MgSO_4$, 1.2; glucose, 10; and $NaHCO_3$, 24.8. Organ bath solutions were aerated with 95% $O_2$/5% $CO_2$ and maintained at 37° C. Tissues were placed under an optimal force of 4 grams and equilibrated for one hour with washes every 15 minutes. Changes in force were recorded and analyzed by a Biopac MP100 (World Precision Instruments, Sarasota, Fla.) data acquisition system via Sensotec (model MBL 5514-02) transducers (Sensotec Inc. Columbus, Ohio).

All tissues were initially challenged with KCl (67 mM) to establish viability. Concentration-response curves were generated in a cumulative fashion and are reported as a percentage of an initial KCl contraction (67 mM) produced in each tissue. Vehicle, β-estradiol, 14 or 16 were added to the tissues 60 minutes prior to initiating the concentration-response curves to agonists. In studies with BayK 8644, tissues were exposed to 10 mM KCl prior to initiating the concentration-response curves for BayK 8644. Only one agonist concentration-response curve was generated in each tissue. All results are expressed as mean±SE where n represents the number of rings examined.

Chemicals

5-HT, acetylcholine, norepinephrine, U46619, and β-estradiol were purchased from Sigma Chemical Co. (St. Louis, Mo.). BayK 8644 was purchased from Research Biochemicals Inc. (Wayland, Mass.). Diltiazem, nifedipine, nitrendipine, and compound nos. 14 and 16 (hereinafter 14 and 16) were synthesized in the Lilly Research Laboratories (Indianapolis, Ind.).

Results

The contractile response of rat aorta to norepinephrine, serotonin and the thromboxane mimetic, U46619 was clearly dependent upon the endothelium (FIG. 1). For each agonist, the contractile response was greater in the absence of the endothelium suggesting that the contractile response was modulated by relaxant agonist(s) released from the endothelium.

Figure 2:
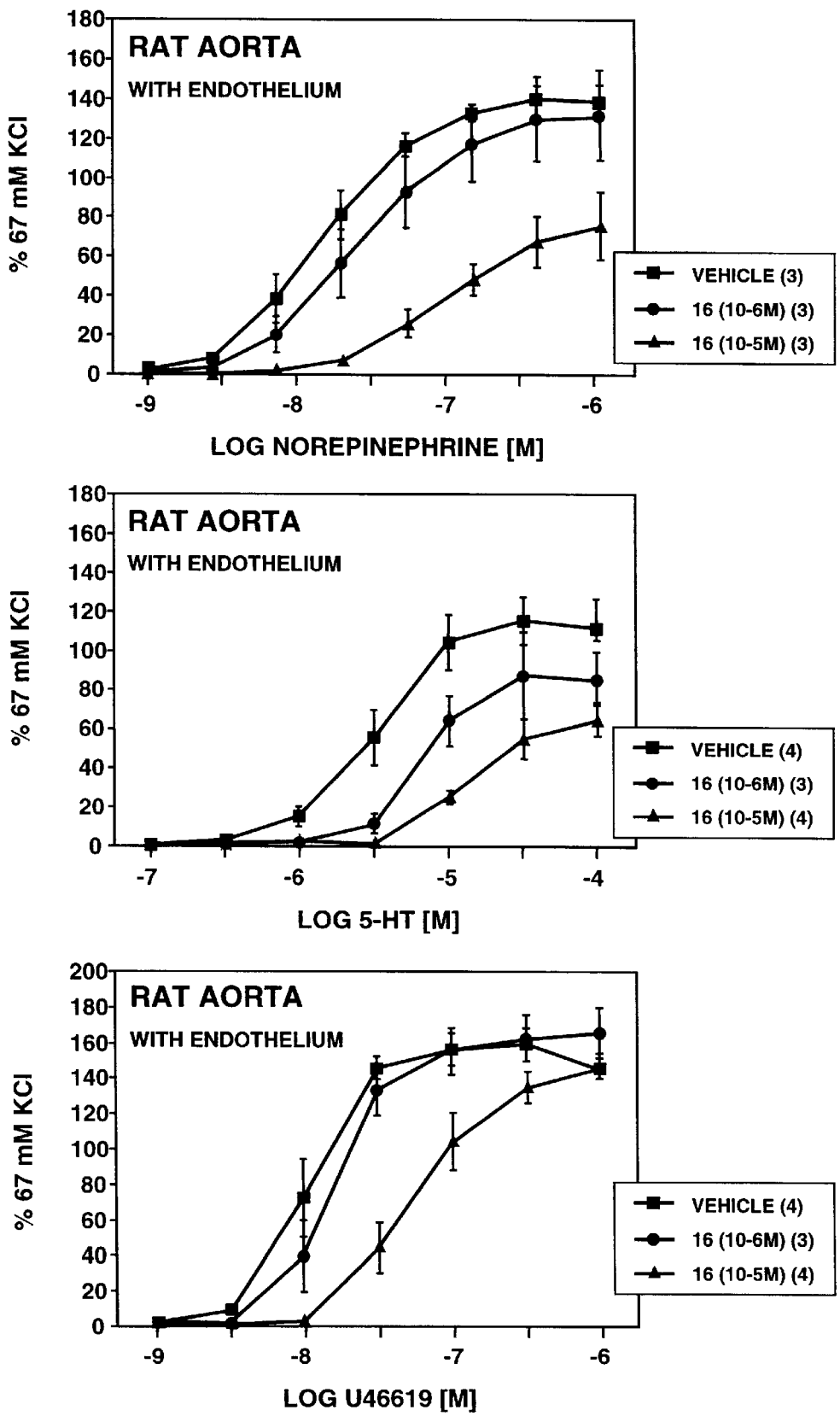
FIG. 2: Effect of 16 on the contractile response to norepinephrine (top), serotonin (middle), and U46619 (bottom) in rat aorta possessing an intact endothelium. Points are mean values and vertical bars represent the standard error of the mean for the number of rings indicated in parenthesis.
Figure 3:
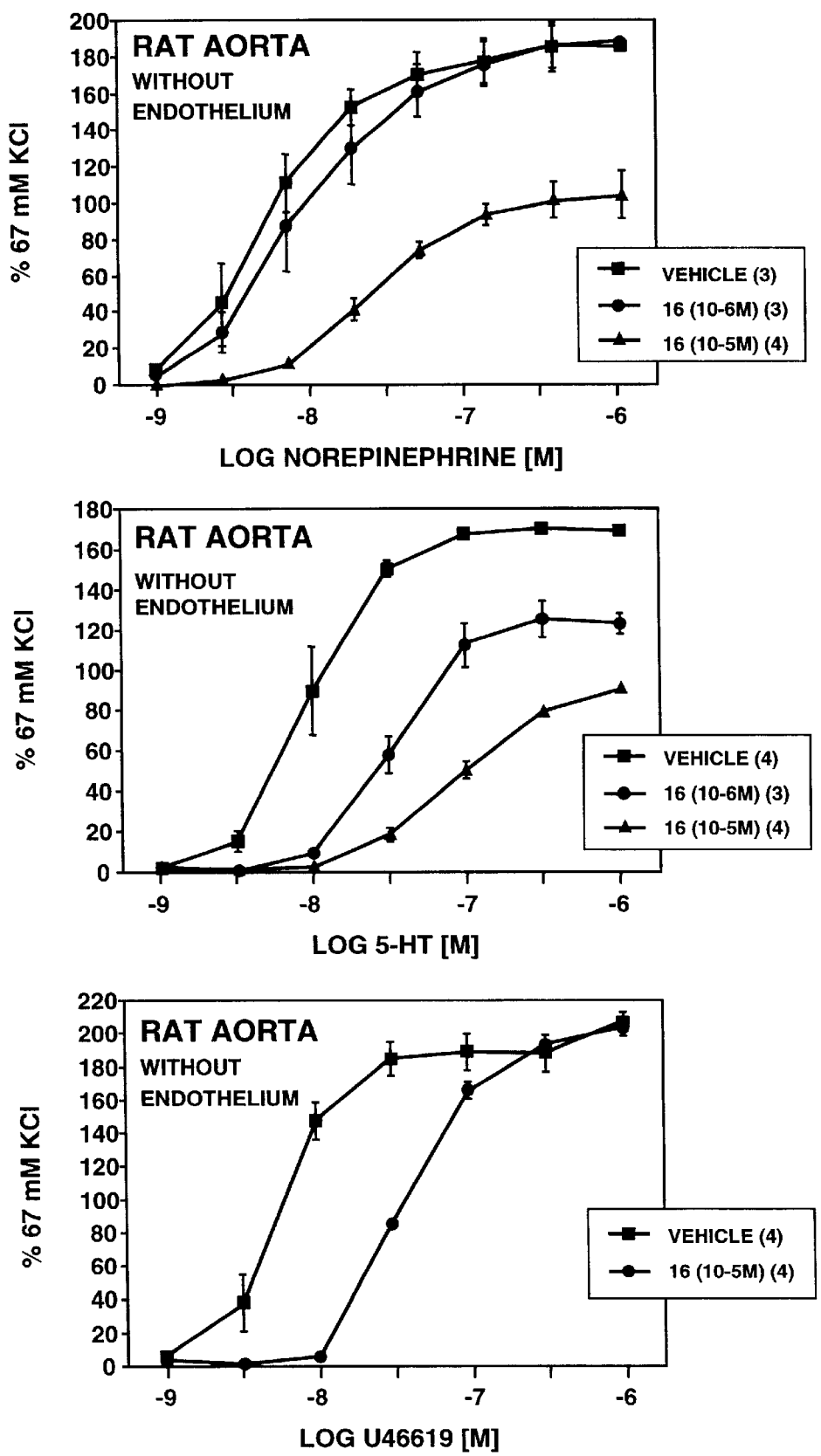
FIG. 3: Effect of 16 on the contractile response to norepinephrine (top), serotonin (middle), and U46619 (bottom) in rat aortic rings without an intact endothelium. Points are mean values and vertical bars represent the standard error of the mean for the number of rings indicated in parenthesis.

The non-steroidal benzothiophene derivative 16 ($10^{-6}$ and $10^{-5}$M) potently inhibited contractile responses to norepinephrine, serotonin and U46619 in rat aorta, and the inhibition of the contractile response appeared independent of the endothelium (FIGS. 2 and 3). As seen previously with β-estradiol, 16 was more potent in inhibiting the contractile response to serotonin relative to norepinephrine or U46619.

Figure 4:
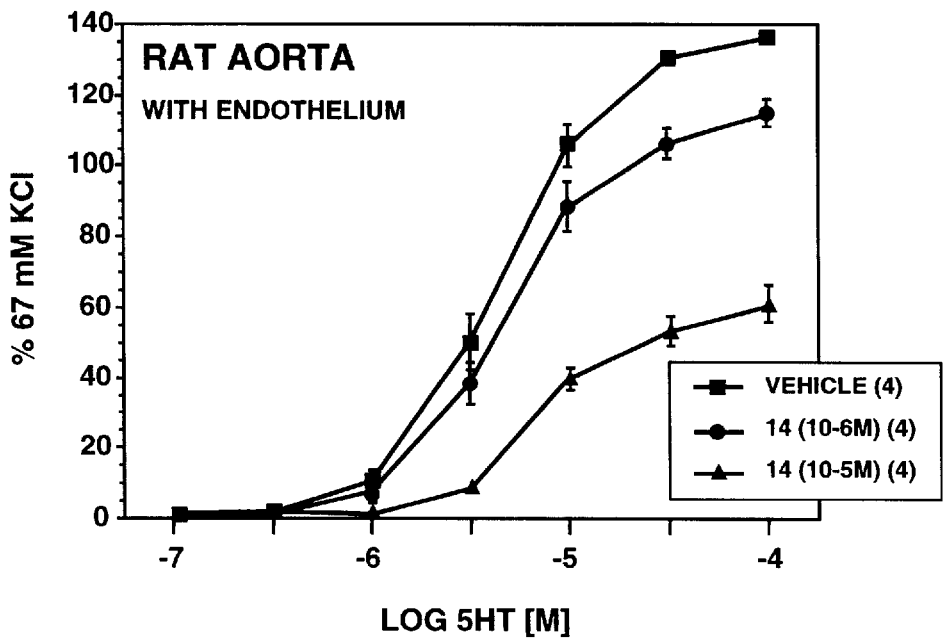
FIG. 4: Effect of 14 on the contractile response to serotonin in rat aorta with (top) and without (bottom) an intact endothelium. Points are mean values and vertical bars represent the standard error of the mean for the number of rings indicated in parenthesis.
Figure 4:
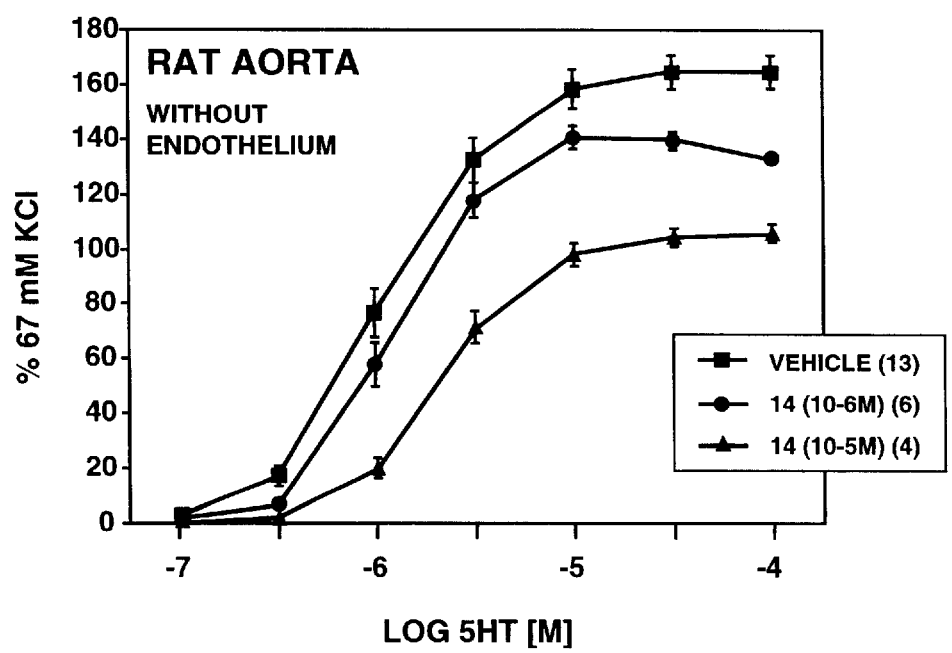
Figure 5:
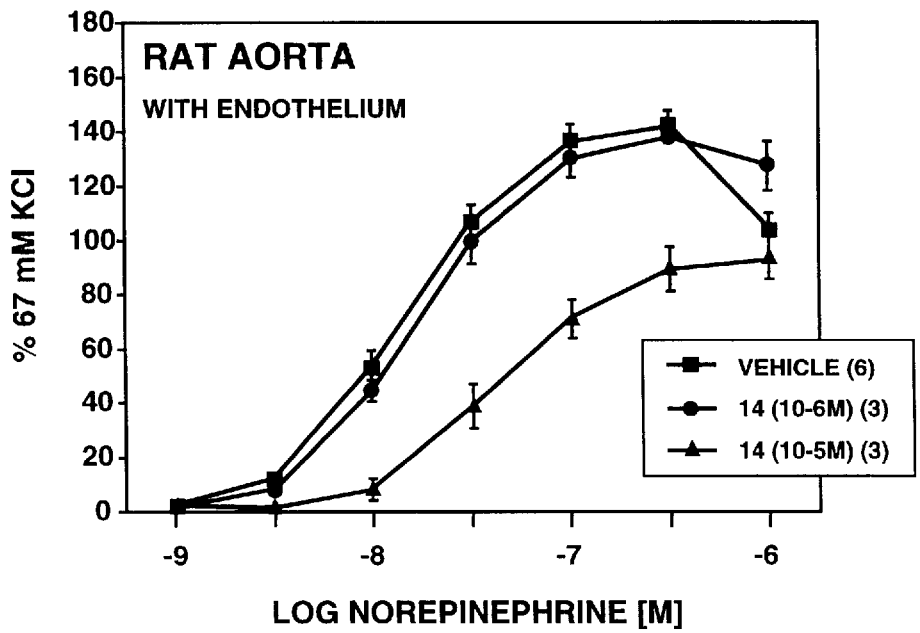
FIG. 5: Effect of 14 on the contractile response to norepinephrine in rat aortic rings with (top) and without (bottom) an intact endothelium. Points are mean values and vertical bars represent the standard error of the mean for the number of rings indicated in parenthesis.
Figure 5:
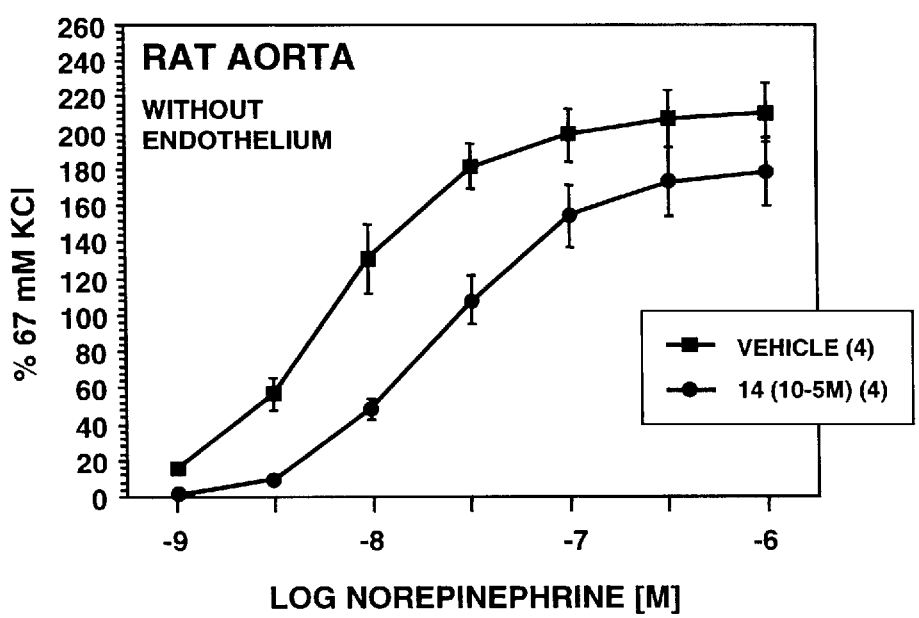
Figure 6:
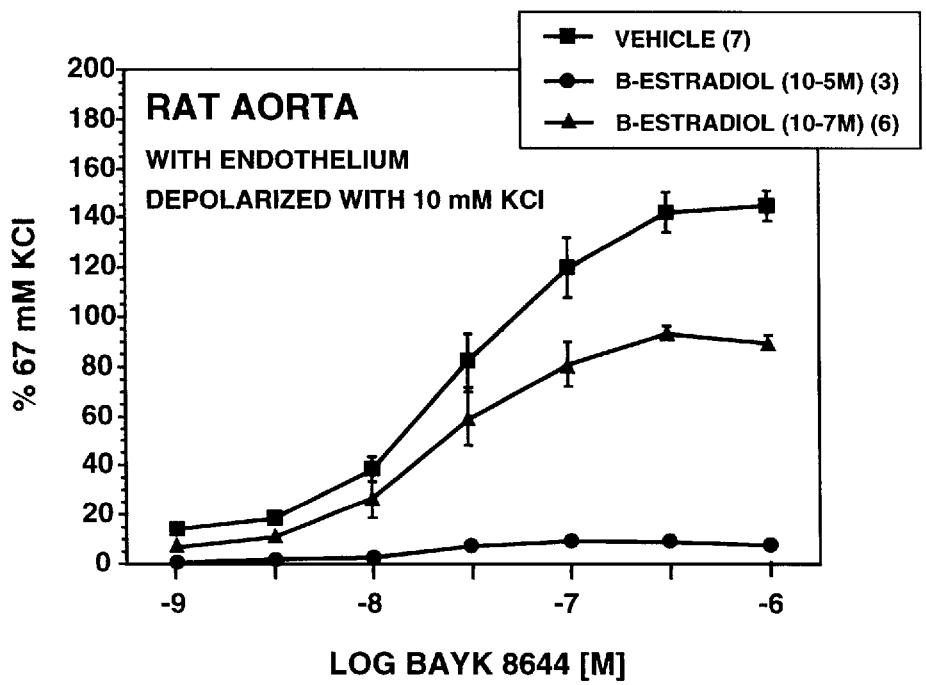
FIG. 6: Effect of β-estradiol (top) and 16 (bottom) on the contractile response of rat aorta possessing an intact endothelium to BayK 8644. Points are mean values and vertical bars represent the standard error of the mean for the number of tissues indicated in parenthesis.
Figure 6:
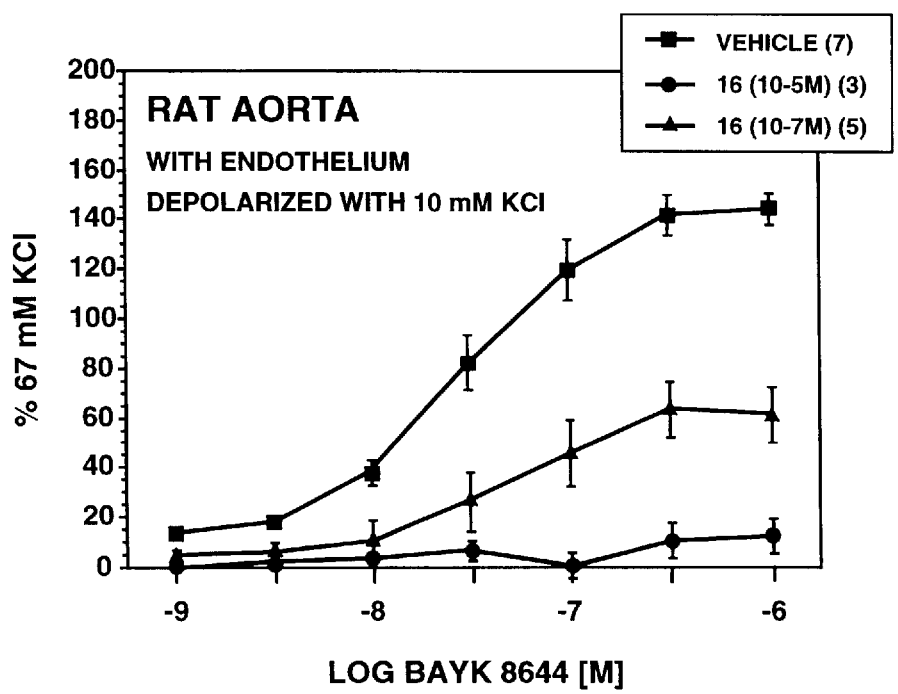

As with 16, 14 also inhibited contractible responses to serotonin (FIG. 4), an inhibition that was greater than with norepinephrine (FIG. 5); effects that were independent of an intact endothelium.

Serotonin-induced contraction is known to utilize extracellular calcium via voltage dependent calcium channels, whereas vascular contraction to norepinephrine is more heavily dependent upon the activation of phosphoinositide turnover and the utilization of intracellular stores of calcium. Thus, contractions to serotonin are more sensitive to inhibition by calcium channel antagonists than contractions to norepinephrine. Cohen and Berkowitz, BLood Vessels, 13, 139–154 (1976); and Gouw et al., *Naunyn-Schmiedeberg's Arch. Pharmacol.*, 339, 533–539 (1989). Because 14 and 16 appeared to exert greatest effectiveness to inhibit serotonin-induced contractile responses, 14 and 16 may be acting as a calcium channel antagonist. For this reason, the effectiveness of both 14 and 16 to inhibit contractile responses induced by the calcium agonist BayK 8644 was examined. See Brown et al., *Nature,* 311, 570–572 (1984).

Figure 7:
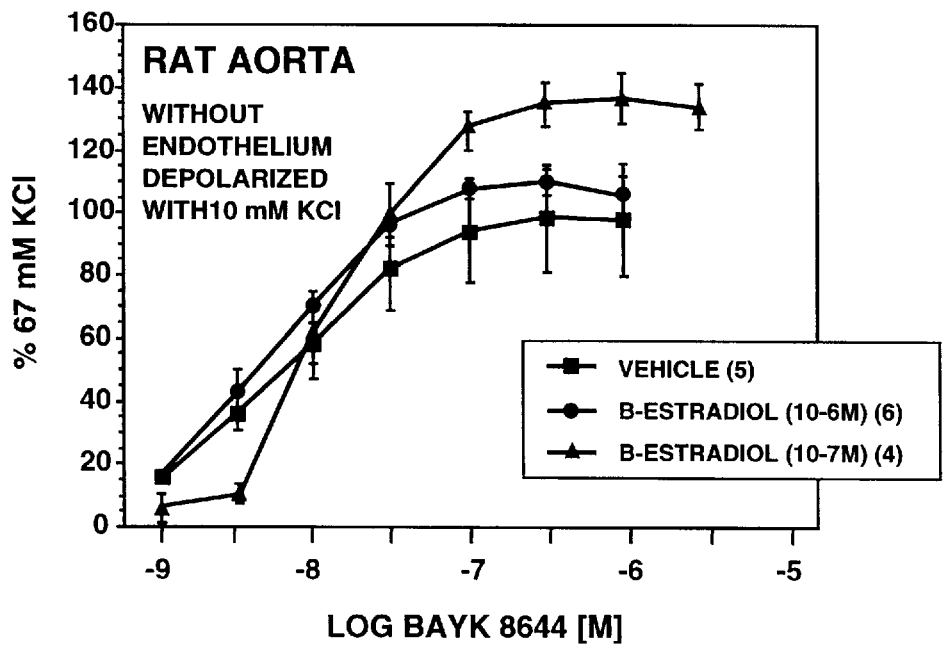
FIG. 7: Effect of β-estradiol (top) and 16 (bottom) on the contractile response of rat aorta without an intact endothelium to BayK 8644. Points are mean values and vertical bars represent the standard error of the mean for the number of tissues indicated in parenthesis.
Figure 7:
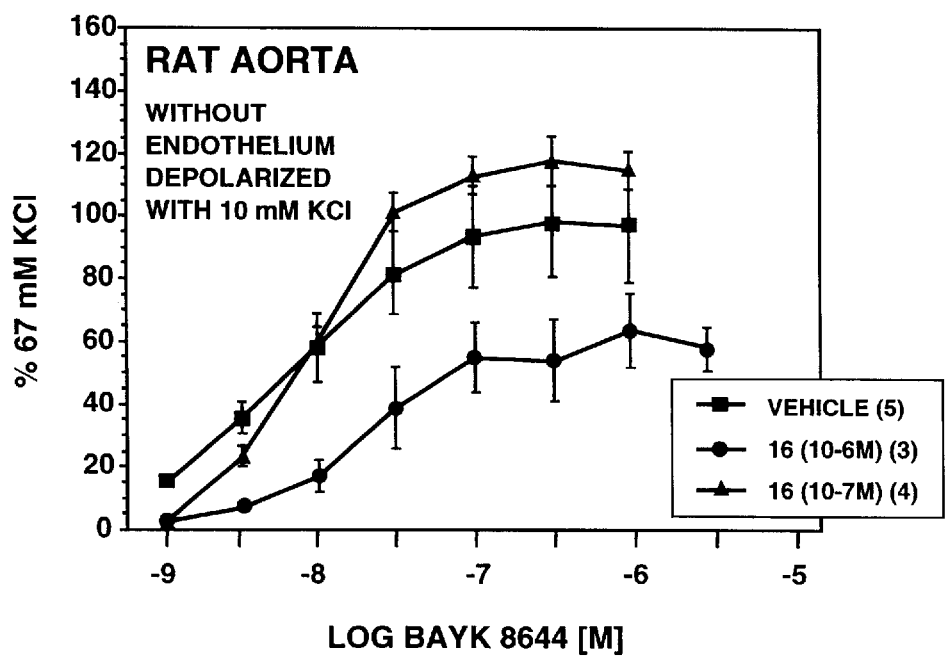
Figure 8:
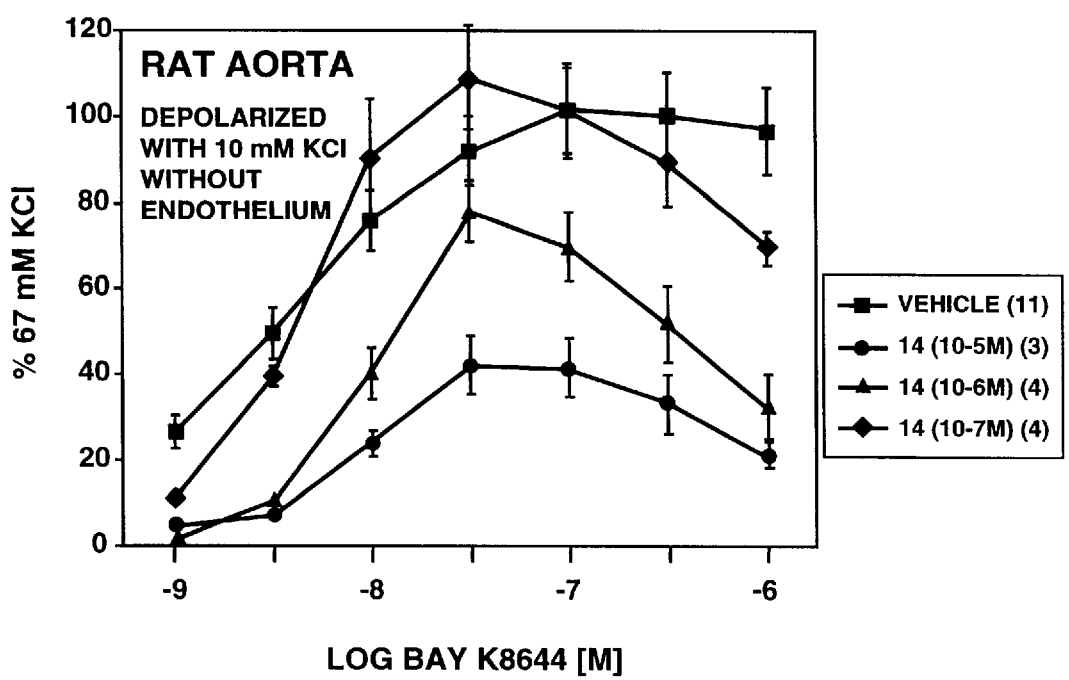
FIG. 8: Effect of 14 ($10^{-6}$ and $10^{-7}$M) on the contractile response to BayK 8644 in rat aorta lacking an endothelium. Points are mean values and vertical bars represent the standard error of the mean for the number of tissues indicated in parenthesis.

In the absence of an intact endothelium, inhibition of the contraction to BayK 8644 occurred with 14 and 16 (FIGS. 7 and 8). These data with BayK 8644 document inhibition of the contractile response to this calcium agonist by both 14 and 16.

Discussion

The ability of estrogen to block calcium channels may contribute to the beneficial effects of estrogen when used as replacement therapy in post-menopausal women. Estrogen is known to possess calcium channel antagonist activity, an effect that has been observed in rabbit and pig coronary arteries.

Recently, several groups have attempted to identify compounds that might mimic the beneficial hemodynamic effects of estrogen while minimizing the uterotropic or undesirable effects of estrogen when used as replacement therapy. In this regard, a series of partial agonist compounds of the benzothiophene structure have been described, of which 14 and 16 are examples. Although 14 and 16 possess similar affinity for the estrogen receptor as 17 hydroxy β-estradiol, little is known regarding vascular effects. Uchiumi et al., *Intl. J. Cancer,* 47, 80–85 (1991). We demonstrate that 14 and 16 can antagonize vascular contractile responses induced by the calcium agonist BayK 8644 documenting calcium channel antagonist activity. In this regard, 16 was more potent than 14, a conclusion consistent with their ability to inhibit contraction to the calcium agonist BayK 8644 and their marked inhibitory effect on contractile responses to norepinephrine, serotonin, and U46619.

The calcium channel antagonist activity of 14 and 16 is probably unrelated to their ability to bind to the estrogen receptor for several reasons. First, both compounds had similar affinity at the estrogen receptor (Uchiumi et al., 1991) and yet 16 was considerably more potent as a calcium channel antagonist than 14. Second, the ability to inhibit contractile responses occurred acutely in these studies suggesting that a nuclear event was not required.

Thus, the present studies establish an acute in vitro effect of 14 and 16 to inhibit calcium channels in vascular tissue using the rat aorta by demonstrating inhibition of BayK-8644 induced contraction, an effect independent of the endothelium. Benzothiophene derivative 16 which binds with similar affinity to the estrogen receptor as 17β-estradiol, is a more potent calcium channel antagonist in vascular tissue than estrogen. Further, these comparative studies provide additional data to support the contention that the calcium channel blockade by 14 and 16 is unrelated to the ability of these agents to bind to the estrogen receptor. If calcium channel inhibition contributes to the clinical effects of estrogen, than 14 and 16 may have some important advantages relative to estrogen as replacement therapy in post-menopausal women.

I claim:

1. A method for treating cardiac disorders by antagonizing or blocking calcium channels in vascular tissue which comprises administering to a warm-blooded animal in need thereof a pharmaceutically-effective amount of a compound having the formula

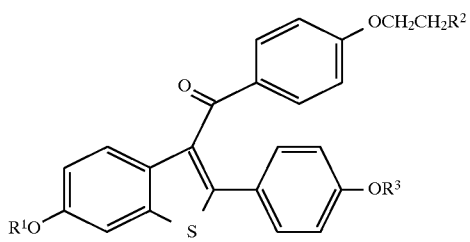

wherein $R^1$ and $R^3$ are independently hydrogen, $C_1$–$C_4$ alkyl, —CO—($C_1$–$C_6$ alkyl), or —$CH_2$Ar, —CO—Ar, wherein Ar is phenyl or substituted phenyl;

$R^2$ is selected from the group consisting of pyrrolidine, hexamethylenemino, and piperidino; or a pharmaceutically-acceptable salt thereof.

2. The method of claim 1 wherein $R^1$ and $R^3$ are hydrogen and $R^2$ is piperidino or pyrrolidino.

3. The method of claim 1 wherein said pharmaceutically-acceptable salt is the hydrochloride salt.

4. The method of claim 1 wherein the cardiac disorder is variant angina, exertional angina, unstable angina, ischemia-reperfusion injury to the myocardium, and arrhythmias.

5. A method for treating cerebral vascular disorders by antagonizing or blocking calcium channels in vascular tissue which comprises administering to a warm-blooded animal in need thereof a pharmaceutically-effective amount of a compound having the formula

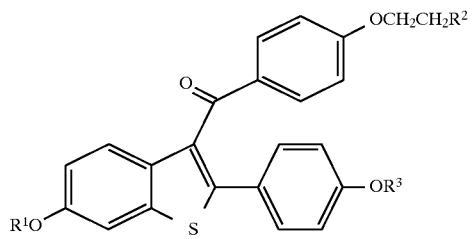

wherein $R^1$ and $R^3$ are independently hydrogen, $C_1$–$C_4$ alkyl, —CO—($C_1$–$C_6$ alkyl), or —$CH_2$Ar, —CO—Ar, wherein Ar is phenyl or substituted phenyl;

$R^2$ is selected from the group consisting of pyrrolidine, hexamethylenemino, and piperidino; or a pharmaceutically-acceptable salt thereof.

6. The method of claim 5 wherein $R^1$ and $R^3$ are hydrogen and $R^2$ is piperidino or pyrrolidino.

7. The method of claim 5 wherein said pharmaceutically-acceptable salt is the hydrochloride salt.

8. The method of claim 5 wherein the cerebral vascular disorder is cerebral vasospasm due to arterial rupture, stroke, and migraine headache.

9. A method for treating renal disorders by antagonizing or blocking calcium channels in vascular tissue which comprises administering to a warm-blooded animal in need thereof a pharmaceutically-effective amount of a compound having the formula

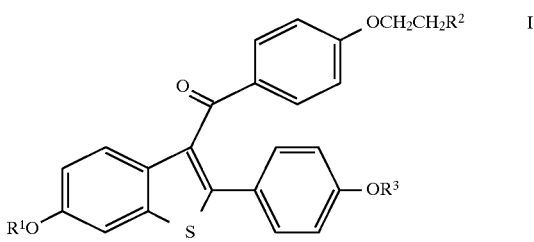

wherein $R^1$ and $R^3$ are independently hydrogen, $C_1$–$C_4$ alkyl, —CO—($C_1$–$C_6$ alkyl), or —$CH_2$Ar, —CO—Ar, wherein Ar is phenyl or substituted phenyl;

$R^2$ is selected from the group consisting of pyrrolidine, hexamethylenemino, and piperidino; or a pharmaceutically-acceptable salt thereof.

10. The method of claim 9 wherein $R^1$ and $R^3$ are hydrogen and $R^2$ is piperidino or pyrrolidino.

11. The method of claim 9 wherein said pharmaceutically-acceptable salt is the hydrochloride salt.

12. A method for treating gastrointestinal disorders by antagonizing or blocking calcium channels in vascular tissue which comprises administering to a warm-blooded animal in need thereof a pharmaceutically-effective amount of a compound having the formula

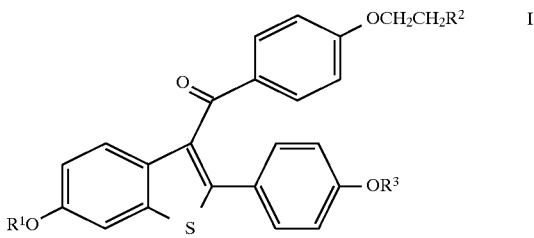

wherein $R^1$ and $R^3$ are independently hydrogen, $C_1$–$C_4$ alkyl, —CO—($C_1$–$C_6$ alkyl), or —$CH_2$Ar, —CO—Ar, wherein Ar is phenyl or substituted phenyl;

$R^2$ is selected from the group consisting of pyrrolidine, hexamethylenemino, and piperidino; or a pharmaceutically-acceptable salt thereof.

13. The method of claim 12 wherein $R^1$ and $R^3$ are hydrogen and $R^2$ is piperidino or pyrrolidino.

14. The method of claim 12 wherein said pharmaceutically-acceptable salt is the hydrochloride salt.

* * * * *